(12) United States Patent
Hadba et al.

(10) Patent No.: US 7,998,466 B2
(45) Date of Patent: Aug. 16, 2011

(54) BIOCOMPATIBLE TISSUE SEALANTS AND ADHESIVES

(75) Inventors: Ahmad R. Hadba, Wallingford, CT (US); Nadya Belcheva, Middletown, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 1287 days.

(21) Appl. No.: 11/635,294

(22) Filed: Dec. 6, 2006

(65) Prior Publication Data

US 2007/0128152 A1 Jun. 7, 2007

Related U.S. Application Data

(60) Provisional application No. 60/742,939, filed on Dec. 6, 2005.

(51) Int. Cl.
*A61K 31/74* (2006.01)
(52) U.S. Cl. .................................. 424/78.02
(58) Field of Classification Search .............. 424/78.02, 424/78.06
See application file for complete search history.

(56) References Cited

U.S. PATENT DOCUMENTS

| | | |
|---|---|---|
| 3,773,595 A | 11/1973 | Burba et al. |
| 3,879,493 A | 4/1975 | Mudde |
| 3,903,232 A | 9/1975 | Wood et al. |
| 4,057,535 A | 11/1977 | Lipatova et al. |
| 4,061,662 A | 12/1977 | Marans et al. |
| 4,132,839 A | 1/1979 | Marans et al. |
| 4,169,175 A | 9/1979 | Marans et al. |
| 4,321,350 A | 3/1982 | Lehmann |
| 4,323,491 A | 4/1982 | Veselovsky et al. |
| 4,404,296 A | 9/1983 | Schapel |
| 4,425,472 A | 1/1984 | Howard et al. |
| 4,451,627 A | 5/1984 | Frisch, Jr. et al. |
| 4,477,604 A | 10/1984 | Oechsle, III |
| 4,511,626 A | 4/1985 | Schumacher |
| 4,547,561 A | 10/1985 | Wegner |
| 4,654,409 A | 3/1987 | Shirai et al. |
| 4,681,934 A | 7/1987 | Shibanai et al. |
| 4,722,815 A | 2/1988 | Shibanai |
| 4,740,534 A | 4/1988 | Matsuda et al. |
| 4,762,899 A | 8/1988 | Shikinami |
| 4,804,691 A | 2/1989 | English et al. |
| 4,806,614 A | 2/1989 | Matsuda et al. |
| 4,829,099 A | 5/1989 | Fuller et al. |
| 4,883,837 A | 11/1989 | Zabrocki |
| 4,994,208 A | 2/1991 | McBain et al. |
| 4,994,542 A | 2/1991 | Matsuda et al. |
| 4,997,656 A | 3/1991 | Shikinami et al. |
| 5,065,752 A | 11/1991 | Sessions et al. |
| 5,082,663 A | 1/1992 | Konishi et al. |
| 5,166,300 A | 11/1992 | Rumon et al. |
| 5,169,720 A | 12/1992 | Braatz et al. |
| 5,173,301 A | 12/1992 | Itoh et al. |
| 5,175,228 A | 12/1992 | Wang et al. |
| 5,204,110 A | 2/1993 | Cartmell et al. |
| 5,346,981 A | 9/1994 | Sarpeshkar et al. |
| 5,374,704 A | 12/1994 | Muller et al. |
| 5,389,718 A | 2/1995 | Potter et al. |
| 5,457,141 A | 10/1995 | Matsuda |
| 5,462,536 A | 10/1995 | Braatz et al. |
| 5,574,104 A | 11/1996 | Kolycheck et al. |
| 5,574,123 A | 11/1996 | Bock et al. |
| 5,578,662 A | 11/1996 | Bennett et al. |
| 5,603,798 A | 2/1997 | Bhat |
| 5,672,652 A | 9/1997 | Bhat |
| 5,688,860 A | 11/1997 | Croft |
| 5,717,030 A | 2/1998 | Dunn et al. |
| 5,780,573 A | 7/1998 | Iwata et al. |
| 5,791,352 A | 8/1998 | Reich et al. |
| 5,795,633 A | 8/1998 | Yokoyama et al. |
| 5,869,566 A | 2/1999 | Thomas |
| 5,900,473 A | 5/1999 | Acevedo et al. |
| 5,912,193 A | 6/1999 | Iwata et al. |
| 5,922,809 A | 7/1999 | Bhat et al. |
| 5,948,427 A | 9/1999 | Yamamoto et al. |
| 5,976,305 A | 11/1999 | Bhat et al. |
| 5,990,237 A | 11/1999 | Bentley et al. |
| 6,071,530 A | 6/2000 | Polson |
| 6,103,850 A | 8/2000 | Reichel et al. |
| 6,154,089 A | 11/2000 | Rombach |
| 6,162,241 A | 12/2000 | Coury et al. |
| 6,197,915 B1 | 3/2001 | Yamana et al. |
| 6,217,894 B1 | 4/2001 | Sawhney et al. |
| 6,235,815 B1 | 5/2001 | Loercks et al. |
| 6,261,544 B1 | 7/2001 | Coury et al. |
| 6,290,729 B1 | 9/2001 | Slepian et al. |
| 6,296,908 B1 | 10/2001 | Reihs et al. |
| 6,297,349 B1 | 10/2001 | Goldberg et al. |
| 6,312,725 B1 | 11/2001 | Wallace et al. |

(Continued)

FOREIGN PATENT DOCUMENTS

EP   0 077 192 A2   4/1983

(Continued)

OTHER PUBLICATIONS

Fessenden Fessenden,Organic Chemistry, 1998, Brooks/Cole, 6th ed. p. 670.*

(Continued)

*Primary Examiner* — Michael G Hartley
*Assistant Examiner* — James Rogers

(57) ABSTRACT

The disclosure relates to compositions for medical/surgical synthetic adhesives and sealants. Adhesive compositions include a functionalized triol and functionalized diol, while sealant compositions further include a multifunctionalized polyol and at least one amine cross linker.

22 Claims, No Drawings

U.S. PATENT DOCUMENTS

| | | |
|---|---|---|
| 6,352,710 B2 | 3/2002 | Sawhney et al. |
| 6,395,112 B1 | 5/2002 | Sitzmann et al. |
| 6,395,823 B1 | 5/2002 | Brink et al. |
| 6,461,631 B1 | 10/2002 | Dunn et al. |
| 6,465,001 B1 | 10/2002 | Hubbell et al. |
| 6,465,004 B1 | 10/2002 | Rossi-Montero et al. |
| 6,495,127 B1 | 12/2002 | Wallace et al. |
| 6,512,033 B1 | 1/2003 | Wu |
| 6,555,645 B1 | 4/2003 | Ikeda et al. |
| 6,565,969 B1 | 5/2003 | Lamon et al. |
| 6,566,406 B1 | 5/2003 | Pathak et al. |
| 6,576,702 B2 | 6/2003 | Anderle et al. |
| 6,579,952 B1 | 6/2003 | Niki et al. |
| 6,582,713 B2 | 6/2003 | Newell et al. |
| 6,605,666 B1 | 8/2003 | Scholz et al. |
| 6,824,703 B2 | 11/2004 | Lawrey et al. |
| 2002/0028875 A1 | 3/2002 | Anderle et al. |
| 2003/0012734 A1 | 1/2003 | Pathak et al. |
| 2003/0032734 A1 | 2/2003 | Roby |
| 2003/0035786 A1 | 2/2003 | Hendriks et al. |
| 2003/0044380 A1 | 3/2003 | Zhu et al. |
| 2003/0162841 A1 | 8/2003 | Pathak et al. |
| 2003/0176615 A1 | 9/2003 | Lawrey et al. |
| 2003/0195293 A1 | 10/2003 | Lubnin et al. |
| 2004/0019178 A1 | 1/2004 | Gross et al. |
| 2004/0023842 A1 | 2/2004 | Pathak et al. |
| 2004/0068078 A1 | 4/2004 | Milbocker |
| 2004/0092695 A1 | 5/2004 | Hu et al. |
| 2004/0198901 A1 | 10/2004 | Graham et al. |
| 2004/0198944 A1 | 10/2004 | Meltzer et al. |
| 2004/0242831 A1 | 12/2004 | Tian et al. |
| 2004/0259968 A1 | 12/2004 | Krebs |
| 2005/0004661 A1 | 1/2005 | Lewis et al. |
| 2005/0069573 A1 | 3/2005 | Cohn et al. |
| 2005/0070913 A1 | 3/2005 | Milbocker et al. |
| 2005/0129543 A1 | 6/2005 | Milbocker et al. |
| 2005/0131192 A1 | 6/2005 | Matsuda et al. |
| 2005/0142162 A1 | 6/2005 | Hunter et al. |
| 2005/0147647 A1 | 7/2005 | Glauser et al. |
| 2005/0154148 A1 | 7/2005 | Nakamichi et al. |
| 2005/0266086 A1 | 12/2005 | Sawhney |

FOREIGN PATENT DOCUMENTS

| | | |
|---|---|---|
| EP | 0 482 467 A2 | 4/1992 |
| EP | 0 488 629 A1 | 6/1992 |
| EP | 0 301 516 B1 | 9/1992 |
| EP | 1 391 205 A1 | 2/2005 |
| EP | 1 719 530 A | 11/2006 |
| EP | 1857489 A1 | 11/2007 |
| GB | 985 144 | 3/1965 |
| JP | 6263850 | 9/1994 |
| JP | 2002060341 | 2/2002 |
| WO | WO 00/43050 A1 | 7/2000 |
| WO | WO 01/00246 A | 1/2001 |
| WO | WO 01/16210 A | 3/2001 |
| WO | WO 02/056790 A2 | 7/2002 |
| WO | WO 03/011173 A2 | 2/2003 |
| WO | WO 03/011173 A3 | 2/2003 |
| WO | WO 2004/039323 A2 | 5/2004 |
| WO | WO 2004/039323 A3 | 5/2004 |
| WO | WO 2004/039857 A1 | 5/2004 |
| WO | WO 2004/041890 A1 | 5/2004 |
| WO | WO 2005/032461 A2 | 4/2005 |
| WO | WO 2005/100429 A1 | 10/2005 |
| WO | WO 2006/010278 A1 | 2/2006 |
| WO | WO 2006/084911 A2 | 8/2006 |
| WO | WO 2006/107957 A2 | 10/2006 |
| WO | WO 2006/128742 A2 | 12/2006 |
| WO | WO 2006/128918 A1 | 12/2006 |
| WO | WO 2007/001448 A2 | 1/2007 |
| WO | WO 2007/067623 A | 6/2007 |
| WO | WO 2008/047100 A1 | 4/2008 |

OTHER PUBLICATIONS

International Search Report from PCT/US06/47013 dated Oct. 3, 2007.
International Search Report from PCT/US06/46558 dated Nov. 9, 2007.
International Search Report from PCT/US06/46552 dated Nov. 15, 2007.
International Search Report from PCT/US06/47023 dated Nov. 21, 2007.
European Search Report (EP 06 00 9170).
Margolin A L et al.: "Steroselective Oligomerizations Catalyzed by Lipases in Organic Olvents"; Tetrahedron Letters, vol. 28, No. 15, 1987pp. 1607-1610.
Okumura S. et al.: "Synthesis of Ester Oligomer by AspergillNiger Lipase" Agricultural and Biological Chemistry, vol. 48, No. 11, 1984, pp. 2805-2808.
Lumann N R et al.: The convergent Synthesis of Poly(glycerol-succininc acid) Dendritic Marcomolecules: Chemistry—A European Journal, VCH Publishers, US vol. 9, 2003, pp. 5618-5626.
Database WPI, Section Ch, Week 199442 Derwent Publications Ltd. London, GB; Class A23, AN 1994-3383493.
Nivasu V M et al.: "In Situ Polymerizable Polyethyleneglycol Containing Polyesterpolyol Acrylates for Tissue Sealant Applications"; Biomaterials 2004 United Kingdom, vol. 25, No. 16, 2004, pp. 3283-3291.
Moon S-Y et al.: Polyurethane/Montorillonite Nancomposites Prepared From Crystalline Polyols, Using 1, 4-Butanediol and Organoclay Hybrids as Chain Extenders: European Polymer Journal, Pergamon Press Ltd. Oxford, GB,; vol. 40, No. 8, Aug. 2004; pp. 1615-16213.
M. J. Song, et al.: "Thermosensitive Sol-Gel Transition Behaviors of Poly(ethylene oide)/ Aliphatic Polyester/Poly(ethylene Oxide) Aqueous Solutions"; Journal of Polymer Science Part A: Polymer Chemistry, vol. 42, No. 3.; Feb. 1, 2004; pp. 772-784.
Mei Xuan Xu et al.: Synthesis and Properties of Unsaturated Polyester Dio-Polyurethanehybrid Polymer Network: Journal of Applied Polymer Science, John Wiley and Sons Inc. New York, US , vol. 54, No. 11, Dec. 12, 1994, pp. 1659-1663.
Oprea S. et al.: "Poly(urethane-methacrylates)s. Synthesis and Characterization"; Polymer, Elsevier Science Publishers B.V., GB, vol. 42, No. 17, Aug. 2001, pp. 7257-7266.
European Search Report for Appln. No. EP 08 25 1790.5 completed Jun. 19, 2009.
European Search Report for Appln. No. EP 08 25 3647 completed Mar. 6, 2009.
International Search Report from Application No. PCT/US08/60971 dated Jul. 18, 2008.
International Search Report from European Application No. EP 06 84 4894 date of completion Jun. 9, 2010.
International Search Report from European Application No. EP 06 84 4890 date of completion Jun. 4, 2010.
International Search Report (PCT/US06/46554 dated Oct. 31, 2007).
International Search Report from Application EP 07 00 1213 dated Sep. 6, 2007.
International Search Report from Application EP 03 77 9244 dated Sep. 26, 2007.
International Search Report from Application PCT/US2006/46553 dated Oct. 31, 2007.
International Search Report from Application PCT/US2006/46554 dated Oct. 31, 2007.

* cited by examiner

BIOCOMPATIBLE TISSUE SEALANTS AND ADHESIVES

CROSS-REFERENCE TO RELATED APPLICATIONS

This application claims the benefit of U.S. Provisional Patent Application No. 60/742,939 filed Dec. 6, 2005, the entire disclosure of which is incorporated by reference herein.

TECHNICAL FIELD

The present disclosure relates to adhesives and sealants formed from synthetic components for medical and surgical use with animal tissues in vivo.

BACKGROUND OF RELATED ART

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that in order for surgical adhesives to be accepted by surgeons, they should possess various properties. For example, they should exhibit high initial tack and an ability to bond rapidly to living tissue; the strength of the bond should be sufficiently high to cause tissue failure before bond failure; the adhesive should form a bridge, typically a permeable flexible bridge; and the adhesive bridge and/or its metabolic products should not cause local histotoxic or carcinogenic effects.

Several materials useful as tissue adhesives or tissue sealants are currently available. One type of adhesive that is currently available is a cyanoacrylate adhesive. However, there is the possibility that a cyanoacrylate adhesive can degrade to generate undesirable by-products such as formaldehyde. Another disadvantage with cyanoacrylate adhesives is that they can have a high flexural modulus which can limit their usefulness.

Another type of tissue sealant that is currently available utilizes components derived from bovine and/or human sources. For example, fibrin sealants are available. However, as with any natural material, variability in the material is frequently observed and, because the sealant is derived from natural proteins, there may be viral transmission concerns.

It would be desirable to provide a biological adhesive or sealant that is fully synthetic and therefore highly consistent in its properties without the concern of viral transmission. Such a composition should be flexible and biocompatible and should be suitable for use as an adhesive or sealant.

SUMMARY

The disclosed compositions relate to synthetic adhesives and sealants for medical/surgical use. The biocompatible adhesive compositions include a functionalized triol and a functionalized diol, while the sealant compositions further include a multifunctional polyol and at least one amine cross linker. In particularly useful embodiments, the triol and diol may be functionalized with a polyalkylene oxide having multiple isocyanate groups.

In embodiments, the compositions of the present disclosure may include biocompatible adhesives including
a functionalized triol of formula

[X—Y—X—O]$_3$—R; and a functionalized diol of formula

[X—Y—X—O]$_2$—R;

wherein X is a diisocyanate, Y is a polyalkylene oxide, and R can be alcohols, aliphatic polyesters, ketones, carbonates, anhydrides, and combinations thereof.

In other embodiments, compositions of the present disclosure may include biocompatible sealants including a functionalized triol of formula

[X—Y—X—O]$_3$—R;

a functionalized diol of formula

[X—Y—X—O]$_2$—R;

a multifunctional alcohol; and at least one amine cross linker, wherein X is a diisocyanate, Y is a polyalkylene oxide, and R can be alcohols, aliphatic polyesters, ketones, carbonates, anhydrides, and combinations thereof. In embodiments, the multifunctional alcohol may be of the formula E-X—Z—[(D)$_w$—X]$_r$, wherein E is a hydrophilic polymer, X can be the same or different at eachlocation and is a diisocyanate, Z is a polyol, D is a bioabsorbable group, w is a number from 1 to 20, and r is a number 1 to 10. Suitable amine cross linkers include primary amines, diamines, aromatic amines, polyamines, ane polyamidoamines.

These compositions can be applied by a variety of methods, including spraying the compositions onto a surgical site. In embodiments, the present disclosure includes methods for closing wounds by applying a composition of the present disclosure to a wound and allowing the composition to set, thereby closing said wound. Such wounds may include, in embodiments, incisions. Compositions of the present disclosure may also be utilized to seal leaks in animal. In embodiments, compositions of the present disclosure may be utilized to adhere a medical device, such as an implant, to a surface of animal tissue.

DETAILED DESCRIPTION

The present disclosure relates to biocompatible compositions for use as tissue adhesives or sealants, which are biocompatible, non-immunogenic and biodegradable. The biocompatible compositions can be employed to adhere tissue edges, adhere medical devices (i.e. implants) to tissue, seal air/fluid leaks in tissues, and for tissue augmentation such as sealing or filling voids or defects in tissue. Thus, as used herein, an "adhesive" is understood to mean a composition which adheres one thing to another, such as tissue edges to each other or a device, such as an implant, to tissue, and a "sealant" is understood to mean a composition which is applied to tissue and utilized to seal air/fluid leaks in tissue or seal or fill small voids or defects in tissue. The biocompatible compositions can be applied to living tissue and/or flesh of animals, including humans.

While certain distinctions may be drawn between the usage of the terms "flesh" and "tissue" within the scientific community, the terms are used interchangeably herein as referring to a general substrate upon which those skilled in the art would understand the present composition to be utilized within the medical field for the treatment of patients. As used herein, "tissue" may include, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic or ascite tissue.

The first component of the biocompatible compositions of the present disclosure includes a functionalized triol. Examples of polyols which may be utilized to form functionalized triols in accordance with the present disclosure include, but are not limited to, polyether polyols; polyester polyols; block copolymers composed of branched chain ethoxylated alcohols; alkoxylated alcohols such as NEODOL® which is sold commercially by Shell Chemical Company; polyvinyl alcohols; polyhydric alcohols; carboxylic acid esters of polyhydric alcohols; polyglycols; and polylactone polyols.

In some embodiments, suitable polyols for use as the functionalized triol include polyether-based polyols, polyester-based polyols such as polycaprolactone-based polyols, and polyhydric alcohols such as glycerol, pentaerythritol, sorbitol, trimethylol propane and diethylene glycol. In some embodiments, the triol can be glycerol, trimethylol propane, hexane-1,2,6-triol, or polycaprolactone triol.

The functionalized triol may include degradable linkages so as to render the triol degradable. Suitable degradable linkages which can be optionally incorporated in the functionalized triol include, but are not limited to, hydrolytically labile α-hydroxy acids such as lactic acid, glycolic acid, and hydroxy-butyric acid, glycolide, lactide, lactones including ε-caprolactone, carbonates such as trimethylene carbonate, ester ethers such as dioxanones including 1,4-dioxane-2-one and 1,3-dioxane-2-one, diacids including succinnic acid, adipic acid, sebacic acid, malonic acid, glutaric acid, azelaic acid, phosphoesters such as ethyl dichlorophosphate, anhydrides including sebacic acid anhydride and azelaic acid anhydride, etc. and combinations thereof. Those skilled in the art will readily envision reaction schemes for incorporating these degradable linkages into the functionalized triol.

Methods for functionalizing such compounds are known to those skilled in the art. In one embodiment, each hydroxy group of the triol is functionalized. In some embodiments, the triol can be functionalized with an isocyanate. Suitable isocyanates for functionalizing the triol include aromatic, aliphatic and alicyclic isocyanates, including polyisocyanates. Examples include, but are not limited to, aromatic diisocyanates such as 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenyl isocyanate), or 2,4,6-trimethyl-1,3-phenylene diisocyanate; aliphatic diisocyanates such as tetramethylxylylene diisocyanate, tetramethylene diisocyanate, hexamethylene diisocyanate, lysine diisocyanate, 2-methylpentane-1,5-diisocyanate, 3-methylpentane-1,5-diisocyanate, or 2,2,4-trimethylhexamethylene diisocyanate; and alicyclic diisocyanates such as isophorone diisocyanate, cyclohexane diisocyanate, hydrogenated xylylene diisocyanate, hydrogenated diphenylmethane diisocyanate, or hydrogenated trimethylxylylene diisocyanate.

In some embodiments, isocyanates for functionalizing such triols include, but are not limited to, toluene diisocyanate (TDI), 4,4'-diphenylmethane diisocyanate (MDI), hexane-1,6-diisocyanate (HDI), isophorone diisocyanate (IPDI), hexamethylene diisocyanate (HMDI), m-tetramethylxylylene diisocyanate (m-TMXDI), p-tetramethylxylylene diisocyanate (p-TMXDI), and combinations thereof.

In some embodiments it may be desirable to form an adduct of a diisocyanate with a hydrophilic polymer such as ethylene glycol or polyethylene glycol and use the resulting adduct to functionalize a triol in accordance with the present disclosure. The adduct may be formed by reacting the diisocyanate with a hydrophilic polymer such as a polyalkylene oxide ("PAO"). Suitable polyalkylene oxides include polyethylene glycol ("PEG"), polyethylene oxide ("PEO"), polypropylene oxide ("PPO"), polyethylene glycols with lactide linkages, polypropylene glycol ("PPG"), polypropylene glycol-co-polyethylene oxide block or random copolymers, and poloxamers such as polyethylene oxide (PEO) copolymers with polypropylene oxide (PPO) such as the triblock PEO-PPO copolymers commercially available as PLURONICS® from BASF Corporation (Mt. Olive, N.J.). In another embodiment, a polyvinyl alcohol ("PVA") may be utilized instead of PAO.

In one embodiment, the adduct may first be prepared and then added to the triol to produce the functionalized triol of the present disclosure. In this embodiment, the adduct can be formed by reacting an excess of a diisocyanate with the polyalkylene oxide to form an isocyanate terminated adduct as exemplified by the following scheme:

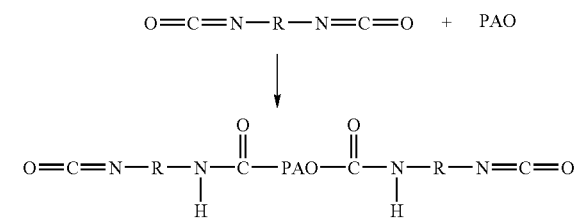

The isocyanate terminated adduct may then be reacted with a triol to produce a functionalized triol of the formula:

[X—Y—X—O]$_3$—R  (I)

where X can be the same or different and is an isocyanate, including a polyisocyanate; Y can be a polyalkylene oxide; and R is an alcohol, aliphatic polyester, ketone, carbonate, anhydride, or a combination thereof. In embodiments, X is hexamethylene diisocyanate, Y is polyethylene glycol, and R is a lactone such as a polycaprolactone.

Where the functionalized triol is a polycaprolactone triol, the triol can have a molecular weight from about 200 g/mol to about 1500 g/mol, in embodiments from about 250 g/mol to about 1300 g/mol.

This first component can be utilized by itself or in combination with a second component to form a surgical adhesive in accordance with the present disclosure. Where utilized, the second component can be a functionalized diol which can have the basic structure of:

[X—Y—X—O]$_2$—R  (II)

where X, Y and R are as defined above. In embodiments, X is an isocyanate such as hexamethylene diisocyanate, Y is a polyethylene glycol, and R is a polycaprolactone.

Where utilized, the functionalized diol can be present in an adhesive composition in an amount from about 10 to about 98 percent by weight of the composition, in embodiments from about 25 to about 95 percent by weight of the composition, typically from about 50 to about 90 percent by weight of the composition. The balance of the adhesive composition in such a case will be the first component, i.e., the functionalized triol, which can be from about 90 to about 2 percent by weight of the composition, in embodiments from about 75 to about 5 percent by weight of the composition, typically from about 50 to about 10 percent by weight of the composition.

In some embodiments, the weight ratio of the first component to the second component in the composition of the present disclosure is about 1:9. In such a case, the resulting adhesive composition will possess a branched structure with the functionalized triol, such as polycaprolactone triol, at the center and the functionalized diols branching out from said triol.

The resulting adhesive composition of the present disclosure can be used in a medical/surgical capacity in place of, or in combination with, sutures, staples, clamps and the like.

Optional components may be added to the composition to adjust its viscosity according to a specific application of use, e.g., as an adhesive or a sealant. Such optional components can include, for example, diethylene glycol dimethyl ether ("DIGLYME"), dimethylformamide ("DMF"), anhydrides such as maleic anhydride, and combinations thereof. Thickening agents which can be used to adjust the viscosity of the compositions of the present disclosure include polycyanoacrylates, polylactic acid, polyglycolic acid, lactic-glycolic acid copolymers, poly-3-hydroxybutyric acid, polyorthoesters, polyanhydrides, pectin, and combinations thereof.

Where utilized, such additives can be included so that they are present in an amount from about 1 to about 30 percent by weight of the composition, in embodiments from about 2 to about 15 percent by weight of the composition.

Optionally, stabilizers can also be added to the first and/or second component to increase the storage stability of the compositions of the present disclosure. Suitable stabilizers can include those which prevent premature polymerization such as quinones, hydroquinone, hindered phenols, hydroquinone monomethyl ether, catechol, pyrogallol, benzoquinone, 2-hydroxybenzoquinone, p-methoxy phenol, t-butyl catechol, butylated hydroxy anisole, butylated hydroxy toluene, or t-butyl hydroquinone. Suitable stabilizers can also include anhydrides, silyl esters, sultones (e.g., α-chloro-α-hydroxy-o-toluenesulfonic acid-γ-sultone), sulfur dioxide, sulfuric acid, sulfonic acid, sulfurous acid, lactone, boron trifluoride, organic acids, alkyl sulfate, alkyl sulfite, 3-sulfolene, alkylsulfone, alkyl sulfoxide, mercaptan, alkyl sulfide and combinations thereof. In some embodiments, an anhydride such as maleic anhydride, sebacic acid anhydride, and/or azelaic acid anhydride, can be used as a stabilizer.

Where utilized, such stabilizers can be included so that they are present in an amount from about 0.01 to about 10 percent by weight of the composition, in embodiments from about 0.1 to about 2 percent by weight of the composition.

In some embodiments, solid supported catalysts may be used during synthesis to improve stability of the resulting adhesive composition. The presence of such catalysts may increase reactivity during use. Suitable catalysts are known to those skilled in the art and can include stannous octoate, triethylamine, diethylaminoethanol, and dimethylaminopyridine (DMAP). The amount of catalyst employed can be from about 0.5 grams to about 50 grams per kilogram of the other components of the composition.

The adhesive composition of the present disclosure can be used for a number of different human and animal medical applications including, but not limited to, wound closure (including surgical incisions and other wounds), adhesives for medical devices (including implants), void fillers, and embolic agents. These adhesives may be used to bind tissue together either as a replacement of, or as a supplement to, sutures, staples, tapes and/or bandages. Use of the disclosed adhesive can eliminate or substantially reduce the number of sutures normally required during current practices, and eliminate the subsequent need for removal of staples and certain types of sutures. The compositions of the present disclosure thus can be particularly useful for use with delicate tissues where sutures, clamps or other conventional tissue closure mechanisms may cause further tissue damage.

The adhesive composition of the present disclosure can be dispensed from a conventional adhesive dispenser, which typically provides mixing of the first and second components prior to the dispenser. Such dispensers are disclosed, for example, in U.S. Pat. Nos. 4,978,336, 4,361,055, 4,979,942, 4,359,049, 4,874,368, 5,368,563, and 6,527,749, the disclosures of each of which are incorporated herein by reference.

In other embodiments, especially where the adhesive composition of the present disclosure is to be utilized as a void filler or to fill a defect in an animal's body, it may be advantageous to more precisely control the conditions and extent of cross-linking; in such a case, it may be desirable to partially cross-link the composition prior to its use to fill a void in animal tissue. The composition of the present disclosure may then be applied to the void or defect and allowed to set, thereby filling the void or defect.

To effectuate the joining of two tissue edges, the two edges are approximated, and the functionalized triol is applied optionally in combination with the functionalized diol. The component(s) crosslink rapidly, generally taking less than one minute. The composition of the present disclosure can thus be used as an adhesive to close a wound, including a surgical incision. In such a case, the composition of the present disclosure can be applied to the wound and allowed to set, thereby closing the wound.

In another embodiment, the present disclosure is directed to a method for using the adhesive composition of the present disclosure to adhere a medical device to tissue, rather than secure two edges of tissue. In some embodiments, depending on the composition of the medical device, a coating may be required on the medical device. In some aspects such a coating can include the functionalized triol of the present disclosure, optionally in combination with the functionalized diol. In some aspects, the medical device includes an implant. Other medical devices include, but are not limited to, pacemakers, stents, shunts and the like. Generally, for adhering a device to the surface of animal tissue, the composition of the present disclosure can be applied to the device, the tissue surface or both. The device, adhesive composition and tissue surface are then brought into contact with each other and the composition is allowed to set, thereby adhering the device and surface to each other.

The present adhesive can also be used to prevent post surgical adhesions. In such an application, the adhesive composition is applied and cured as a layer on surfaces of internal tissues in order to prevent the formation of adhesions at a surgical site during the healing process. In addition to the formation of adhesion barriers, in embodiments the adhesive may be utilized to form implants such as gaskets, buttresses or pledgets for implantation.

In another embodiment, the adhesive composition can be used to attach skin grafts and position tissue flaps during reconstructive surgery. In still another embodiment, the adhesive can be used to close tissue flaps in periodontal surgery.

Application of the adhesive, with or without other additives, can be done by any conventional means. These include dripping, brushing, or other direct manipulation of the adhesive on the tissue surface, or spraying of the adhesive onto the surface. In open surgery, application by hand, forceps or the like is contemplated. In endoscopic surgery, the adhesive can be delivered through the cannula of a trocar, and spread at the site by any device known in the art.

In alternate embodiments of the present disclosure, the first component, i.e., the functionalized trio, optionally in combination with the second functionalized diol described above, can be reacted with additional components to form a sealant in accordance with the present disclosure. The sealant thus produced can be in the form of a sprayable composition capable of achieving both rapid cure and the formation of an adhesive barrier after application. In this embodiment, the additional components for the sealant can include a multifunctional alcohol such as a multifunctional polyol, and at least one amine cross linker. In some embodiments, this multifunctional alcohol can be formed from a polyol, a hydrophilic polymer, a polyisocyanate, and optionally a bioabsorbable group.

The polyol portion of the multifunctional alcohol can be any biologically acceptable polyol for surgical use (i.e., non-toxic and biodegradable). Suitable polyols can include, for example, sorbitol, glycerol, pentaerythritol, mannitol, glucose, dextrose, sucrose, other polyhydric alcohols, and combinations thereof. In a particularly useful embodiment, sorbitol is used as the polyol of the multifunctional polyol.

In one embodiment, the polyol of the multifunctional alcohol can be functionalized with an adduct. The adduct can include at least one bioabsorbable group that is endcapped with a biocompatible compound. Suitable bioabsorbable groups include hydrolytically labile α-hydroxy acids such as lactic acid, glycolic acid, and hydroxy-butyric acid, glycolide, lactide, lactones including ε-caprolactone, carbonates such as trimethylene carbonate, ester ethers such as dioxanones including 1,4-dioxane-2-one and 1,3-dioxane-2-one, diacids including succinnic acid, adipic acid, sebacic acid, malonic acid, glutaric acid, azelaic acid, phosphoesters such as ethyl dichlorophosphate, anhydrides including sebacic acid anhydride and azelaic acid anhydride, and the like, and combinations thereof. In an embodiment, polylactic acid can be used as the bioabsorbable group.

The bioabsorbable group may be endcapped with an isocyanate. Suitable isocyanates for endcapping the bioabsorbable group include the diisocyanates described above for endcapping the functionalized polyol. In some embodiments, the isocyanate can be a diisocyanate such as toluene diisocyanate (TDI), 4,4'-diphenylmethane diisocyanate (MDI), 1,6-hexamethylene diisocyanate (HMDI), isophorone diisocyanate (IPDI), 4,4'-oxybis(phenyl isocyanate), or lysine diisocyanate.

In an embodiment the multifunctional alcohol may be further functionalized with a second adduct that includes at least one hydrophilic polymer. Suitable hydrophilic polymers are known to those skilled in the art and include those hydrophilic polymers described above for use in preparing the functionalized polyol. In one embodiment, a PAO such as PEG can be utilized as the hydrophilic polymer. In some embodiments, the hydrophilic polymer may be utilized to form an adduct similar to the adduct described above with respect to the functionalized polyol, i.e., the hydrophilic polymer is endcapped with an isocyanate, such as a diisocyanate described above for endcapping the functionalized polyol.

The above constituents can then be combined by mixing or blending by any means known to those skilled in the art. The multifunctional alcohol and adduct(s), thus form a compound of the formula:

E-X—Z—[(D)<sub>w</sub>—X]<sub>r</sub>          (III)

where E is the hydrophilic polymer, X can be the same or different at each location and is an isocyanate as described above, Z is a polyol component, D is a bioabsorbable group, w is a number from 1 to 20, and r is a number from 1 to 10. In a particularly useful embodiment, E is a polyethylene glycol, X is hexamethylene diisocyanate, Z is D-sorbitol, D is lactide, w is a number from 2 to 10 and r is a number from 2 to 5.

The hydrophilic polymer can be lengthened or shortened to modify the viscosity of the multifunctional alcohol, thereby modifying the viscosity and barrier properties of the final sealant composition, as desired.

In embodiments, the above multifunctional polyol may be combined with the functionalized triol, optionally in combination with the diol component described above, in situ in the presence of at least one amine cross linker to form a sealant composition of the present disclosure. Amine cross linkers which may be utilized include primary amines, diamines, aromatic amines, polyamines, polyamidoamines, and combinations thereof. Suitable amines which may be utilized as the amine cross linker include poly(allyl amine), poly(L-lysine), polyalkylene oxides having two or more amine functional groups, triethylamine, diisopropylethylamine (Hünig's base), N,N-dimethylethanolamine, diaminobicyclooctane, N-ethylmorpholine, bis(2-dimethylaminoethyl)ether, N',N'-dimethylpiperazine, N,N,N',N',N'-pentamethyldiethylene triamine, N,N-dimethylcyclohexylamine, N,N-dimethylbenzylamine, N,N-dimethyl(ethylamine), N,N,N',N'',N''-pentamethyl-diproylene triamine, 1-(2-hydroxypropyl)imidazole, dimethyl coconut amine, dimethyl octylamine, dimethyl decylamine, dimethyl laurylamine, dimethylmyristylamine, dimethylpalmitylamine, dimethyl stearyl amine, dimethyl behenyl amine, pyridine, dimethylaminopyridine (DMAP), dimethyl pyridine, and the like.

Other examples of suitable amines for use as the at least one amine cross linker include, but are not limited to, ethylene diamine, hexamethylene diamine, isomers of hexamethylene diamine, diethylene triamine, triethylene tetramine, tetraethylene pentamine, bishexamethylene triamine, N,N'-Bis(3-aminopropyl)-1,2-ethane diamine, N-(3-Aminopropyl)-1,3-propane diamine, N-(2-aminoethyl)-1,3 propane diamine, cyclohexane diamine, isomers of cyclohexane diamine, 4,4'-methylene biscyclohexane amine, 4'4'-methylene bis(2-methylcyclohexanamine), isophorone diamine, and phenalkylene polyamines.

Aromatic amines may also be used as the amine cross linker. Suitable aromatic amines include, for example, di-(4-aminophenyl)sulfone, di-(4-aminophenyl)ether, 2,2-bis(4-aminophenyl)propane, 4,4'-diamino diphenylmethane, 3,3'-dimethyl-4,4'-diaminodiphenyl methane, m-phenylene diamine, p-phenylene diamine, m-xylylene diamine, toluene diamine, 4,4'-methylene dianiline, benzidine, 4,4'-thiodianiline, 4-methoxy-1,3-phenyldiamine, 2,6-diaminopyridine, and dianisidine.

Polyether diamines may also be utilized as the amine cross linker. Suitable polyether diamines include, but are not limited to, 4,9-dioxadodecane-1,12-diamine, 4,7,10-trioxatridecane-1,12-diamine, bis(3-amino propyl)polytetrahydrofurans of varying molecular weights, and commercially available polyoxyalkylene amines from Texaco Chemical Co. under the JEFFAMINE® brand as D230, D400, D2000, T403, and T-3000.

In some embodiments, the amine cross linker can be an amino functional polymer such as those sold under the JEFFAMINE® brand, a poly(allyl amine), poly(L-lysine) or other amino functional polymers such as a polyalkylene oxide, including PEG, PEO and PPO having two or more amine functional groups.

The first component, i.e., the functionalized triol, can be present in the resulting sealant composition in an amount from about 1 to about 50 percent by weight of the composition, in embodiments from about 5 to about 25 percent by weight of the composition.

The second component, i.e., the functionalized diol component, can be present in the resulting sealant composition in an amount from about 97 to about 48 percent by weight of the composition, in embodiments from about 95 to about 75 percent by weight of the composition.

The third component, i.e., the multifunctional polyol, can be present in the resulting sealant composition in an amount from about 1 to about 25 percent by weight of the composition, in embodiments from about 5 to about 15 percent by weight of the composition.

The at least one amine cross linker may be applied in an amount sufficient to enhance the polymerization of the components of the sealant composition which, in some embodiments, can be in an amount from about 1 to about 50 percent by weight of the sealant composition, typically from about 10 to about 25 percent by weight of the sealant composition.

The multifunctional polyol may be combined with the functionalized triol, optionally in combination with the second diol component, and at least one amine cross linker by any means known to those skilled in the art to form a sealant composition of the present disclosure. In embodiments, the multifunctional polyol and functionalized triol, optionally in combination with the second diol component, may be dissolved in a solvent to form a first component solution. Suitable solvents include those that are water miscible and biologically acceptable for medical/surgical use. In some embodiments, the solvents can include DIGLYME (diethylene glycol dimethyl ether), N,N-dimethylformamide ("DMF"), dimethyl sulfoxide, and the like.

The at least one amine cross linker can be dissolved in an aqueous media which contains at least one biodegradable thickener to form a second component solution. Suitable biologically acceptable thickeners include disaccharides, polysaccharides, alginates, hyaluronic acid, pectins, dextrans, cellulosics such as carboxymethyl cellulose, methyl cellulose, and the like.

The first component solution and the second component solution may then be combined upon application to form a sealant composition of the present disclosure. The final sealant composition of the present disclosure has several advantageous properties. The final sealant composition has a rapid curing time. Application of the sealant composition, with or without other additives, can be done by any conventional means. These include dripping, brushing, or other direct manipulation of the sealant on the tissue surface, by syringe, such as with a mixer nozzle, or spraying of the sealant to the surface. Where delicate or spongy tissues are involved and/or air or fluid leaks must be sealed, spray application of a sealant composition may be utilized to avoid stress to the tissue and insure a uniform coating over the area.

In some embodiments, a dual-compartment applicator may be utilized and mixing of the first component solution and second component solution occurs to form a sealant upon dispensing by an aerosol or by means of a mixing head attached to the applicator or syringe. Other additives can be introduced into the first component solution, the second component solution, or both.

The sealant composition may be sprayed onto mammalian tissue, which lowers the risk of additional mechanical stress on the tissue. The spray application can be done by any means known to those skilled in the art such that the sealant composition can be applied as a fine mist or aerosol. For example, the composition can be placed in a spray bottle and delivered with a hand pump. Alternatively, the composition can be placed in a container with a non-chlorofluorohydrocarbon propellant (e.g., air, nitrogen, carbon dioxide, and/or hydrocarbons) and delivered using a pressurized spray can. In either case, the composition is passed through a fine orifice to form a mist and delivered to the surgical location.

The sealant composition can be used in place of, or in combination with, sutures, staples, clamps and the like. Applications for the sealant compositions of the present disclosure include sealing tissues to prevent or control blood or other fluid leaks at suture or staple lines. In embodiments, the sealant composition can be used to seal or adhere delicate tissue together in place of conventional tools that may cause mechanical stress. The sealant composition can also be used to seal air and/or fluid leaks in tissue. Additionally, the sealant composition can be applied to tissue as a barrier to prevent adhesions, provide a protective layer for delicate damaged tissue and/or provide a drug delivery layer to a surgical site.

When used as a sealant, the composition of the present disclosure can be used in surgery to prevent or inhibit bleeding or fluid leakage both during and after a surgical procedure. It can also be applied to prevent air leaks associated with pulmonary surgery. The sealant may be applied directly to the desired area in at least an amount necessary to seal off any defect in the tissue and seal off any fluid or air movement.

While the adhesive compositions of the present disclosure have been described as including a functionalized triol and a functionalized diol, and whereas the sealant compositions of the present disclosure have been described as including a functionalized triol, a functionalized diol, a multifunctional polyol and at least one amine cross linker, it is also contemplated that the adhesive compositions of the present disclosure could be used as sealants and the sealant compositions of the present disclosure could be used as adhesives. Thus, as would be readily apparent to one skilled in the art, the desired properties of the biocompatible compositions of the present disclosure can be adjusted by the selection of the specific components utilized to prepare the resulting adhesive or sealant compositions.

A variety of optional ingredients including medicinal agents may also be added to the biocompatible compositions of the present disclosure. These agents may be added to adhesive compositions of the present disclosure, sealant compositions of the present disclosure, or both. A phospholipid surfactant that provides antibacterial stabilizing properties and helps disperse other materials in the biocompatible compositions may be added to the compositions of the present disclosure. Additional medicinal agents include antimicrobial agents, colorants, preservatives, or medicinal agents such as, for example, protein and peptide preparations, antipyretic, antiphlogistic and analgesic agents, anti-inflammatory agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, antiulcer agents, hypnotics, antibiotics, antifungal agents, sedative agents, bronchodilator agents, antiviral agents and dysuric agents.

Imaging agents such as iodine or barium sulfate, or fluorine, can also be combined with the compositions of the present disclosure to allow visualization of the surgical area through the use of imaging equipment, including X-ray, MRI, and CAT scan.

Additionally, an enzyme may be added to the compositions of the present disclosure to increase their rate of degradation. Suitable enzymes include, for example, peptide hydrolases such as elastase, cathepsin G, cathepsin E, cathepsin B, cathepsin H, cathepsin L, trypsin, pepsin, chymotrypsin, γ-glutamyltransferase (γ-GTP) and the like; sugar chain hydrolases such as phosphorylase, neuraminidase, dextranase, amylase, lysozyme, oligosaccharase and the like; oligonucleotide hydrolases such as alkaline phosphatase, endoribonuclease, endodeoxyribonuclease and the like. In some embodiments, where an enzyme is added, the enzyme may be included in a liposome or microsphere to control the rate of its release, thereby controlling the rate of degradation of the composition of the present disclosure. Methods for incorporating enzymes into liposomes and/or microspheres are known to those skilled in the art.

The present compositions have a number of advantageous properties. The resulting compositions of the present disclosure are safe and biocompatible, possess enhanced adherence to tissue, are biodegradable, have hemostatic potential, have low cost, and are easy to prepare and use. By varying the selection of the polymer components, the strength and elasticity of the adhesive and/or sealant composition can be controlled, as can the gelation time.

The compositions rapidly form a compliant gel matrix, which insures stationary positioning of tissue edges or implanted medical devices in the desired location where the composition is utilized as an adhesive, and a tightly adherent yet flexible seal where the composition is used as a sealant. In either case, the rapidity of gelation lowers the overall required surgical/application time. The compositions exhibit little or no swelling upon gel matrix formation, and therefore retain the positional integrity of the tissue to which the composition is applied and/or location of a medical device. The compositions form strong cohesive bonds, based in part on a low percent of water content as compared to other adhesive and sealant compositions. They exhibit excellent mechanical performance and strength, while retaining the necessary pliability to adhere living tissue. This strength and pliability allows a degree of movement of tissue without shifting the surgical tissue edge. Additionally, the compositions are biodegradable, allowing the degradation components to pass safely through the subject's body.

It will be understood that various modifications may be made to the embodiments disclosed herein. For example, the compositions in accordance with this disclosure can be blended with other biocompatible, bioabsorbable or non-bioabsorbable materials. As another example, optional ingredients such as dyes, fillers, medicaments or antimicrobial compounds can be added to the composition. Therefore, the above description should not be construed as limiting, but merely as exemplifications of typical embodiments. Those skilled in the art will envision other modifications within the scope and spirit of the claims appended hereto.

What is claimed is:

1. A biocompatible adhesive composition comprising:
a functionalized triol of formula

a functionalized diol of formula

wherein X can be the same or different at each location and is a diisocyanate, Y is a polyalkylene oxide, and R is selected from the group consisting of alcohols, aliphatic polyesters, ketones, carbonates, anhydrides, and combinations thereof.

2. A biocompatible adhesive composition as in claim 1, wherein the isocyanate is selected from the group consisting of 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenyl isocyanate), 2,4,6-trimethyl-1,3-phenylene diisocyanate, tetramethylxylylene diisocyanate, tetramethylene diisocyanate, hexamethylene diisocyanate, lysine diisocyanate, 2-methylpentane-1,5-diisocyanate, 3-methylpentane-1,5-diisocyanate, 2,2,4-trimethylhexamethylene diisocyanate, isophorone diisocyanate, cyclohexane diisocyanate, hydrogenated xylylene diisocyanate, hydrogenated diphenylmethane diisocyanate, and hydrogenated trimethylxylylene diisocyanate.

3. A biocompatible adhesive composition as in claim 1, wherein the polyalkylene oxide is selected from the group consisting of polyethylene glycol, polyethylene oxide, polypropylene oxide, polypropylene glycol-co-polyethylene oxide copolymers, and polyethylene oxide copolymers with polypropylene oxide.

4. A biocompatible adhesive composition as in claim 1, wherein the polyalkylene oxide comprises a polyethylene glycol.

5. A biocompatible adhesive composition as in claim 1, wherein the functionalized diol is present in an amount from about 10 to about 98 percent by weight of the composition, and the functionalized triol is present in an amount from about 90 to about 2 percent by weight of the composition.

6. A biocompatible sealant composition comprising:
a functionalized triol of formula

a functionalized diol of formula

a multifunctional alcohol; and
at least one amine cross linker, wherein X can be the same or different at each location and is a diisocyanate, Y is a polyalklene oxide, and R is selected from the group consisting of alcohols, aliphatic polyesters, ketones, carbonates, anhydrides, and combinations thereof.

7. A biocompatible sealant composition as in claim 6, wherein the isocyanate is selected from the group consisting of 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenyl isocyanate), 2,4,6-trimethyl-1,3-phenylene diisocyanate, tetramethylxylylene diisocyanate, tetramethylene diisocyanate, hexamethylene diisocyanate, lysine diisocyanate, 2-methylpentane 1,5-diisocyanate, 3-methylpentane-1,5-diisocyanate, 2,2,4-trimethylhexamethylene diisocyanate, isophorone diisocyanate, cyclohexane diisocyanate, hydrogenated xylylene diisocyanate, hydrogenated diphenylmethane diisocyanate, and hydrogenated trimethylxylylene diisocyanate.

8. A biocompatible sealant composition as in claim 6, wherein the polyalkylene oxide is selected from the group consisting of polyethylene glycol, polyethylene oxide, polypropylene oxide, polypropylene glycol-co-polyethylene oxide copolymers, and polyethylene oxide copolymers with polypropylene oxide.

9. A biocompatible sealant composition as in claim 6, wherein the polyalkylene oxide comprises a polyethylene glycol.

10. A biocompatible sealant composition as in claim 6, wherein the multifunctional alcohol comprises a polyol selected from the group consisting of sorbitol, glycerol, pentaerythritol, mannitol, glucose, dextrose, sucrose, and combinations thereof.

11. A biocompatible sealant composition as in claim 6, wherein the multifunctional alcohol is functionalized with a bioabsorbable group selected from the group consisting of lactic acid, glycolic acid, hydroxy-butyric acid polyhydroxyvaleric acid, glycolide, lactide, ε-caprolactone, trimethylene carbonate, 1,4-dioxane-2-one, 1,3-dioxane-2-one, succinnic acid, adipic acid, sebacic acid, malonic acid, glutaric acid, azelaic acid, ethyl dichlorophosphate, sebacic acid anhydride, azelaic acid anhydride, and combinations thereof.

12. A biocompatible sealant composition as in claim 11, wherein the bioabsorbable group of the multifunctional alcohol is endcapped with an isocyanate selected from the group consisting of toluene diisocyanate, 4,4'-diphenylmethane diisocyanate, 1,6-hexamethylene diisocyanate, isophorone diisocyanate, 4,4-oxybis(phenyl isocyanate), and lysine diisocyanate.

13. A biocompatible sealant composition as in claim 11, wherein the multifunctional alcohol is further functionalized with at least one hydrophilic polymer.

14. A biocompatible sealant composition as in claim 13, wherein the at least one hydrophilic polymer comprises a polyalkylene oxide.

15. A biocompatible sealant composition as in claim 6 wherein the multifunctional alcohol is of the formula

 (III)

wherein E is a hydrophilic polymer, X can be the same or different at each location and is a diisocyanate, Z is a polyol, D is a bioabsorbable group, w is a number from 1 to 20, and r is a number from 1 to 10.

16. A biocompatible sealant composition as in claim 15 wherein the hydrophilic polymer comprises a polyethylene glycol, the isocyanate comprises hexamethylene diisocyanate, the multifunctional polyol comprises D-sorbitol, the bioabsorbable group comprises lactide, w is a number from 2 to 10, and r is a number from 2 to 5.

17. A biocompatible sealant composition as in claim 6, wherein the at least one amine cross linker is selected from the group consisting of primary amines, diamines, aromatic amines, polyamines, and polyamidoamines.

18. A biocompatible sealant composition as in claim 6, wherein the at least one amine cross linker is selected from the group consisting of poly(allyl amine), poly(L-lysine) and polyalkylene oxides having two or more amine functional groups.

19. A biocompatible sealant composition as in claim 6, wherein the functionalized triol is present in an amount from about 1 to about 50 percent by weight of the composition, the functionalized diol is present in an amount from about 48 to about 97 percent by weight of the composition, the multifunctional polyol is present in an amount from about 1 to about 25 percent by weight of the composition, and the at least one amine cross linker is present in an amount from about 1 to about 50 percent by weight of the composition.

20. A method for closing a wound comprising:
applying the biocompatible adhesive composition of claim 1 to said wound; and
allowing the biocompatible adhesive composition to set thereby closing said wound.

21. A method for sealing a leak in animal tissue comprising:
applying the biocompatible sealant composition of claim 6 to said leak; and
allowing the biocompatible sealant composition to set thereby sealing said leak.

22. A method for adhering a medical device to a surface of animal tissue comprising the steps of:
applying the biocompatible adhesive composition of claim 1 to said device, said surface or both;
bringing the device, biocompatible adhesive composition and surface into contact with each other; and
allowing the biocompatible adhesive composition to set thereby adhering the device and surface to each other.

* * * * *

UNITED STATES PATENT AND TRADEMARK OFFICE
CERTIFICATE OF CORRECTION

PATENT NO. : 7,998,466 B2  Page 1 of 1
APPLICATION NO. : 11/635294
DATED : August 16, 2011
INVENTOR(S) : Hadba et al.

It is certified that error appears in the above-identified patent and that said Letters Patent is hereby corrected as shown below:

In claim 1, replace formula (I) with the following:

[X-Y-X–O]$_3$–R;      (I)

In claim 1, replace formula (II) with the following:

[X-Y-X–O]$_2$–R      (II)

Signed and Sealed this
Twenty-fifth Day of October, 2011

David J. Kappos
*Director of the United States Patent and Trademark Office*

UNITED STATES PATENT AND TRADEMARK OFFICE
CERTIFICATE OF CORRECTION

PATENT NO. : 7,998,466 B2  Page 1 of 1
APPLICATION NO. : 11/635294
DATED : August 16, 2011
INVENTOR(S) : Hadba et al.

It is certified that error appears in the above-identified patent and that said Letters Patent is hereby corrected as shown below:

Column 11, line 56 (claim 1, formula (I)) should read:

[X-Y-X–O]$_3$–R;   (I)

Column 11, line 59 (claim 1, formula (II)) should read:

[X-Y-X–O]$_2$–R   (II)

This certificate supersedes the Certificate of Correction issued October 25, 2011.

Signed and Sealed this
Twenty-second Day of November, 2011

David J. Kappos
*Director of the United States Patent and Trademark Office*